(12) United States Patent
Baert et al.

(10) Patent No.: US 9,402,982 B2
(45) Date of Patent: Aug. 2, 2016

(54) MINIMALLY-ADVANCING LUMINAL CATHETER

(75) Inventors: Edward Baert, Melsen (BE); Frank DeWaele, De Pinte (BE)

(73) Assignees: Steerable Instruments BVBA (BE); Universiteit Gent (BE)

( * ) Notice: Subject to any disclaimer, the term of this patent is extended or adjusted under 35 U.S.C. 154(b) by 179 days.

(21) Appl. No.: 14/241,488

(22) PCT Filed: Sep. 5, 2012

(86) PCT No.: PCT/EP2012/067334
§ 371 (c)(1),
(2), (4) Date: Feb. 27, 2014

(87) PCT Pub. No.: WO2013/034602
PCT Pub. Date: Mar. 14, 2013

(65) Prior Publication Data
US 2014/0207044 A1 Jul. 24, 2014

Related U.S. Application Data

(60) Provisional application No. 61/531,312, filed on Sep. 6, 2011.

(30) Foreign Application Priority Data

Sep. 5, 2011 (EP) .................................. 11180066

(51) Int. Cl.
*A61M 5/00* (2006.01)
*A61M 27/00* (2006.01)
*A61M 25/04* (2006.01)

(52) U.S. Cl.
CPC ............. *A61M 27/006* (2013.01); *A61M 25/04* (2013.01)

(58) Field of Classification Search
CPC ............ A61M 27/006; A61M 27/002; A61M 5/14276; A61M 2202/0464; A61M 2210/0693; A61M 2205/8287; A61M 25/04; A61B 5/031
USPC ................................................ 604/8–10, 537
See application file for complete search history.

(56) References Cited

U.S. PATENT DOCUMENTS

| 3,492,996 | A | 2/1970 | Fountain |
| 4,646,752 | A | 3/1987 | Swann |
| 6,264,625 | B1 * | 7/2001 | Rubenstein ......... A61M 27/006 604/537 |
| 2008/0262406 | A1 * | 10/2008 | Wiener ................. A61M 25/04 604/8 |

FOREIGN PATENT DOCUMENTS

WO 2013034602 A1 3/2013

OTHER PUBLICATIONS

International Preliminary Report on Patentability for PCT/EP2012/067334. Dated Mar. 12, 2014. 6 pages.

* cited by examiner

*Primary Examiner* — Philip R Wiest
(74) *Attorney, Agent, or Firm* — Lathrop & Gage LLP; James H. Velema, Esq.

(57) ABSTRACT

The present invention relates to an implantable catheter (100) provided for insertion through a wall (50) of a dural venous sinus (70) in a subject, having a proximal (20) and distal end (30), comprising: —a tubular shaft (10) for insertion through the wall (50) of the venous sinus (70) into the sinus (52), provided with a shaft lumen (12) in fluid connection with a proximal port (14) at the proximal end and a distal port (16) at the distal end of the shaft (10), and —a stop element (40) disposed on an outer surface of the tubular shaft (10), configured to limit the depth of insertion of the tubular shaft (10) into the sinus.

19 Claims, 11 Drawing Sheets

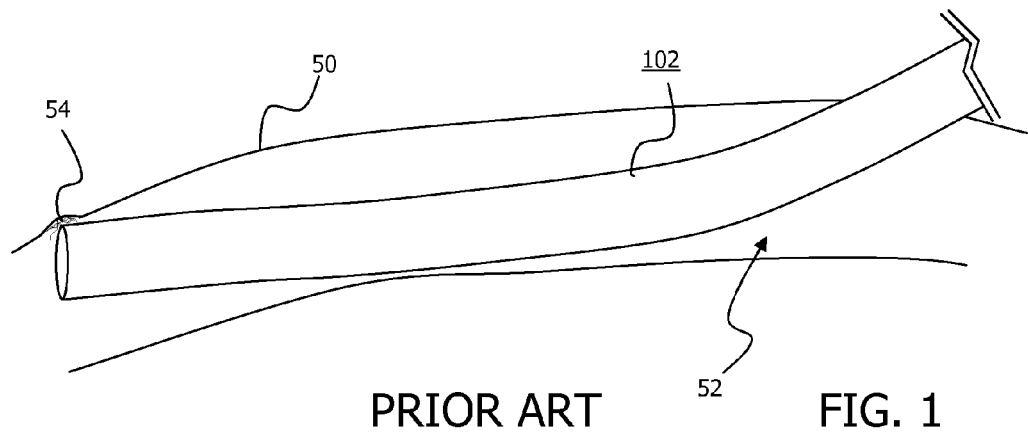
PRIOR ART  FIG. 1
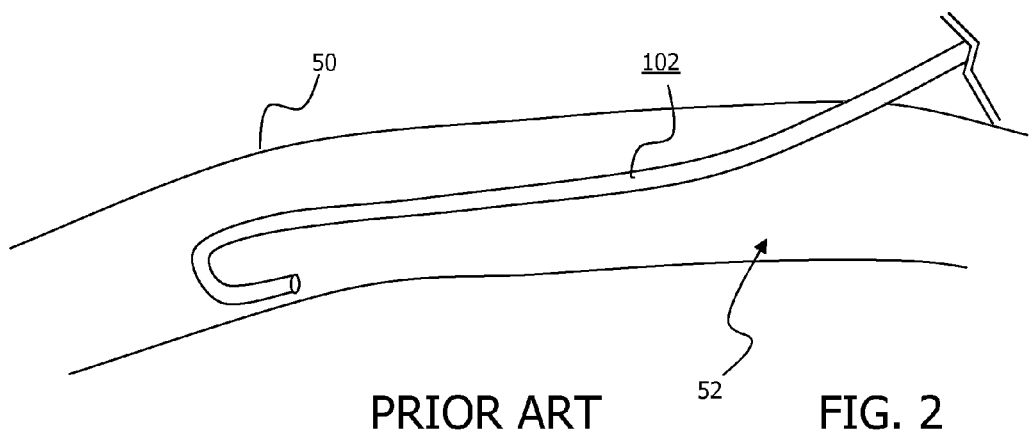
PRIOR ART  FIG. 2

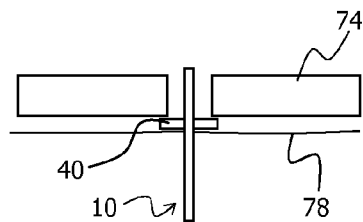
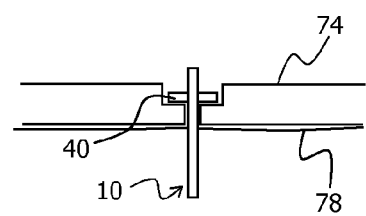
FIG. 15A  FIG. 15B
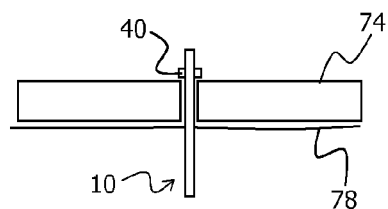
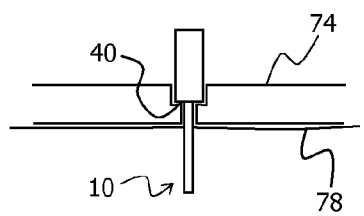
FIG. 15C  FIG. 15D
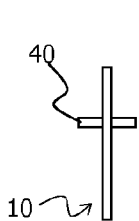
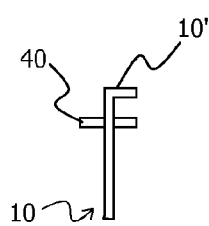
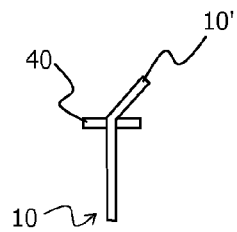
FIG. 16A  FIG. 16B  FIG. 16C

MINIMALLY-ADVANCING LUMINAL CATHETER

RELATED APPLICATIONS

This application is a 35 U.S.C. §371 filing of International Application No. PCT/EP2012/067334, filed Sep. 5, 2012, which claims priority to European Patent Application No. 11180066.0, filed Sep. 5, 2011 and U.S. Patent Application No. 61/531,312, filed Sep. 6, 2011, each of which is incorporated herein by reference in its entirety.

FIELD OF THE INVENTION

The present invention is in the field of medical catheters. More in particular, it is in the field of a catheter incorporated into cerebrospinal fluid (CSF) shunt.

BACKGROUND TO THE INVENTION

A catheter of the prior art may be regarded as having some important technical disadvantages. For instance, the catheter has a relative wide external diameter to facilitate a catheter lumen of sufficient dimension for the flow of fluid, and requires advancement through the vessel lumen. The wide external diameter of the prior art catheter may cause (sub) obstruction of the blood flow. Additionally, the position of the catheter tip cannot be stabilised with respect to the wall of the vessel, causing a risk of dislocation of the catheter's distal tip and possible dysfunction of the catheter.

A further disadvantage of conventional catheters is damage to the vessel wall during advancement. In particular, there may be damage or irritation to the endothelium. While pushing the catheter inside a vessel lumen, the catheter's tip can either cause endothelial wall lesions or friction initiating the cascade of blood clotting, or can be deviated by a septum, causing malfunctioning or obstruction of the catheter.

As conventional catheters are advanced through the venous vessel by maintaining the catheter essentially parallel with the vessel (see FIGS. 1 and 2), clearance around the point of entry is necessary, e.g. a wide diameter burr hole through the cranium in the case of accessing the superior sagittal sinus. In adults, introducing the catheter into the sinus through a standard skull burr hole is technically cumbersome, since an oblique angle is necessary to prevent endothelial laceration of the opposite venous sinus wall and to realize a correct orientation of the catheter (i.e. ante- or retrograde to the blood stream). However, the thickness of the skull bone, requires a wide bore hole to achieve an angle sufficiently oblique. Also, in the pediatric and adult population, the positioning of the subgaleal trajectory of the shunt system is quite difficult in order to prevent kinking of the tubing and to avoid stress causing displacement of the sinusal catheter.

The evacuation of cerebrospinal fluid is necessary to treat medical conditions or illnesses. In particular those in which the physiological evacuation of cerebrospinal fluid is insufficient or disturbed such as in hydrocephalus, normal pressure hydrocephalus, benign intracranial hypertension. It may also be used to treat medical conditions in which the retention or accumulation of substances in the cerebrospinal fluid is caused by or responsible for the disease such as in Alzheimer's disease, Down's syndrome, hereditary cerebral hemorrhage with amyloidosis of the Dutch type (HCHWA-D), epilepsy, narcolepsy, Parkinson's disease, multiple sclerosis or other demyelating disease of the central nervous system, amyotrophic lateral sclerosis, brain tumors, Guillain-Barré syndrome, and the like.

Typically, evacuation of cerebrospinal fluid (CSF) is typically performed using a CSF shunt. CSF shunts in the art commonly comprise three components: (1) a catheter positioned in a cerebral ventricle or cistern, the ventricular catheter; (2) a valve preventing regurgitation of CSF into the ventricles and preventing intracranial hypotension either by exercising resistance to the CSF flow (pressure gradient valves) or by constantly adapting the CSF flow (flow regulating valves); (3) a distal catheter classically being inserted into the right cardiac atrium (atrial catheter) or into the peritoneal cavity (peritoneal catheter). The ventriculo-atrial and ventriculo-peritoneal shunts of the art are disposed with significant disadvantages set out below.

Evacuation of cerebrospinal fluid remains non-physiological. This principally due to the changing orientation of the peritoneal or atrial catheter in the lying state versus in the sitting or erect position of the patient. In the lying position, the fluid column in the distal catheter is in a horizontal orientation, creating no influence on the pressure gradient between the brain's ventricles and the intraperitoneal cavity or cardiac atrium. In the sitting or erect position, the distal catheter is in a vertical orientation. Due to gravity, this fluid column in a vertical orientation exerts the so called siphoning effect. This siphoning effect can cause over-drainage of cerebrospinal fluid causing intracranial hypotension. In the acute stage, this over-drainage can cause collapse of the brain's ventricles and acute subdural hematoma. In the chronic stage this over-drainage can cause (a) chronic (postural) intracranial hypotension with headache and/or nausea and/or vomiting and/or chronic fatigue with concentration problems and intellectual dysfunction and/or visual or auditory disturbances; (b) chronic subdural hematoma; (c) slit ventricle syndrome; (d) iatrogenic craniosynostosis with microcephaly in infants.

In normal individuals, the superior sagittal sinus and the right cardiac atrium are connected by collapsible cervical veins (the internal jugular veins), hence the venous cerebral blood flow is constantly adapted to the position or physiological condition of the normal individual, preventing the siphoning effect. In the ventriculo-atrial and ventriculo-peritoneal shunt patients, the internal jugular veins are bypassed, therefore more complex valves (variable resistance valves or flow regulating valves) and anti-siphon devices are utilised in the art, making a cerebrospinal fluid shunt much more complex, more vulnerable, and more expensive. Despite these technical improvements, a small group of patients still experience symptoms due to non-physiological cerebrospinal fluid evacuation and therefore non-physiological intracranial pressures.

Ventriculo-atrial and ventriculo-peritoneal shunts are easily obstructed causing insufficient cerebrospinal fluid evacuation and therefore intracranial hypertension. Main causes of obstruction are blood clots or brain tissue debris blocking the ventricular catheter or the valve, protein accumulation in the valve mechanism, choroid plexus 'growing' inside the ventricular catheter. The siphoning effect might also be responsible for a great number of the ventricular catheter obstructions by 'aspirating' the choroid plexus into the catheter's lumen. In growing children the catheters can block by kinking or by breaking caused by the increased tension. Also, in growing children, the peritoneal catheter's tip can be retracted into the subcutaneous fat or the atrial catheter's tip into the superior caval vein causing insufficient cerebrospinal fluid evacuation.

Ventriculo-atrial and ventriculo-peritoneal shunts have a high rate of bacterial shunt infections, with risk of bacterial meningitis or ventriculitis or cerebritis, possibly with livelong morbidity or even mortality risk. The infection rates in the implantation period are between three to seven percent.

Because of the vulnerability, complexity and high cost and non-physiological cerebrospinal fluid evacuation of the above mentioned ventriculo-atrial and ventriculo-peritoneal shunt systems, there is a worldwide medical interest for establishing a cerebrospinal fluid shunt between the ventricles or cisterns of the brain and a dural venous sinus (e.g. superior sagittal sinus, transverse sinus, sigmoid sinus). These cerebrospinal fluid shunts are known as ventriculosinus shunts. This is to obtain a physiologically adequate evacuation of cerebrospinal fluid by using the flow regulating effect of the collapsible internal jugular veins. Very important and pioneering in vitro and in vivo experiments and development of surgical techniques have been realized by professor Ismail El-Shafei, M.D. and his son professor Hassan El-Shafei, M.D., in Cairo, Egypt. Since 1985 prof. Ismail El-Shafei advocates and implants the retrograde ventriculo-sagittal sinus shunt. Professor Svend Erik Boergesen, M.D. and professor Flemming Gjerris, M.D. of the University Hospital Rigshospitalet, Copenhagen, Denmark, also developed a cerebrospinal fluid shunt system shunting between the cerebral ventricle and a dural venous sinus, the so-called SinuShunt.

Disadvantages associated with ventriculosinus shunts include their obstructive size that may cause a raised venous pressure inside the dural venous sinus, may reduce the blood flow speed and thus the risk of clotting of the blood inside the dural venous sinus (sinus thrombosis). Typically a catheter that forms part of the prior art shunt will have an external diameter of 2 to 3 millimeter and an intrasinusal length of 20 to 50 millimeter, which may cause a significant obstruction of the blood flow in the accommodating vessel by its large volume (e.g. minimal 1 mm$^2$×π×20 mm or 62.8 mm$^3$ to maximal 1.5 mm$^2$×π×50 mm or 353.25 mm$^3$). Additionally, the catheter cannot be stabilized onto the sinus's wall, causing a risk of dislocation of the catheter's distal tip and possible dysfunction of the cerebrospinal fluid shunt.

Moreover, the position of catheter tip cannot be stabilised inside the sinus's lumen; it should be localised in the center of the sinus's diameter. A catheter's tip lying against the internal wall of the venous sinus has important disadvantages. The catheter is more likely to be blocked by the endothelial layer covering the internal wall of the dural venous sinus, thus causing a total obstruction of the cerebrospinal fluid shunt. Further, the catheter tip lying against the internal wall of the venous sinus cannot fully profit from the impaction effect created by the velocity of the blood flow inside the dural venous sinus as the velocity of this blood flow is maximal at the center of the sinus's diameter and minimal against the sinus's inside wall. This lower velocity of blood flow at the sinus's inside wall, again advocates the clotting of blood at the catheter's tip, blocking the cerebrospinal fluid shunt. Also, a catheter's tip in contact with the endothelial wall activates the blood clotting cascade.

While advancing the catheter inside the dural venous sinus with an intrasinusal length of 20 to 50 millimeter, the catheter's tip can easily either cause endothelial wall lesions increasing the risk of blood clotting, or can be deviated by an intrasinusal septum, causing malfunctioning or obstruction of the cerebrospinal fluid shunt.

Moreover, in the prior art, the surgeon needs to make an incision of a minimal length of 5 millimeter in the wall of the superior sinus to introduce a standard catheter inside the dural venous sinus. This increases the risk of important blood loss, the risk of aspiration of air inside the sinus possibly causing an air embolism and the risk of invagination of the endothelial layer causing obstruction to the blood flow inside the dural venous sinus.

US2008/0262406 describes a secure device for the attachment of a shunt catheter, wherein the secure attachment is to an outside wall of the peritoneal cavity. U.S. Pat. No. 3,492,996 describes a ventriculo-atrial shunt having an attachment means to an atrium of the heart. U.S. Pat. No. 4,646,752 describes an intracranial measuring screw not designed for use in a shunt.

The present invention aims to overcome the disadvantages of the art.

SUMMARY OF SOME EMBODIMENT OF THE INVENTION

The present invention relates to an implantable catheter (100) provided for insertion through a wall (50) of a dural venous sinus (70) in a subject, having a proximal (20) and distal end (30), comprising:
  a tubular shaft (10) for insertion through the wall (50) of the venous sinus (70) into the sinus (52), provided with a shaft lumen (12) in fluid connection with a proximal port (14) at the proximal end and a distal port (16) at the distal end of the shaft (10), and
  a stop element (40) disposed on an outer surface of the tubular shaft (10), configured to limit the depth of insertion of the tubular shaft (10) into the sinus.

The depth of insertion of the tubular shaft (10) may be limited to less than the span of said sinus (52) in transverse cross-section. The depth of insertion of the tubular shaft (10) may be limited to essentially half of the span of said sinus (52). The stop element (40) may incorporate a fixation element (60), configured to fix the position of the tubular shaft (10) relative to the point of insertion into the wall (50) of said sinus (52). The stop element and/or fixation element (60) may be configured for epidural placement. The fixation element (60) may comprise one or more wings (62, 62', 65, 65'). The wings (62, 62') may be expandable wings and comprise springs that maintain the wings open in an uncompressed state. The wings (62, 62') may be configured to expand in the space between the cranium and the dura mater. The insertion depth of the tubular shaft (10) may be limited to avoid contact of the tubular shaft (10) with the inner wall of said sinus (52). The distal port (16) may be provided as a side port on the tubular shaft (10). The distal port (16) may be provided at the terminal end of the tubular shaft (10). The distal port (16) may be provided at the distal terminal end of the tubular shaft (10) that contains at least one bend distal to the stop element (40). An imaginary line drawn through the central axis of the distal port (16) may touch the inner surface of the tubular shaft (10) distal of the stop element (40). The catheter may be configured such that the distal port (16) is oriented to face the direction of blood flow in the sinus (52). The catheter may be incorporated into the sinus end of a ventriculosinus CSF shunt. The sinus may be the superior sagittal sinus, transverse sinuses, or sigmoid sinus. The total length of tubular shaft (10) distal to the stop element (40) may be equal to or less than 15 mm. The drop length (42'—FIG. 4C) of tubular shaft (10) distal to the stop element (40), that is the linear distance from an imaginary plane that contacts maximally the engaging surface of the stop element (40) to the distal end of the tubular shaft (10), measured along an axis perpendicular to said imaginary plane, may be equal to or less than 9 mm. The drop width (42"—FIG. 4D) of tubular shaft (10) distal to the stop element (40), that is the length of the opposite side of right angled triangle, having hypotenuse (h), opposite (o) and adjacent (ad) sides, where the opposite side is opposite angle, a, where the hypotenuse (h) is the linear distance between the distal end of the tubular shaft (10) and the point of contact with the stop element, and angle a is the corner of the triangle at said point of contact, may be equal to or less than 6 mm. The distal port may be provided to one side of the tubular shaft or at the tip of the distal end of the tubular shaft. In the first case, an imaginary line drawn through the central axis of the distal port may touch the inner surface of the tubular shaft distal of the stop element. In the second case, the imaginary line through the central axis of the distal port is parallel and not touching the inner surface of the tubular shaft distal of the stop element.

The invention further relates to the use of a catheter (100) as defined above, for the manufacture of a device for insertion through a wall (50) of a dural venous sinus in a subject (52) wherein the insertion depth of the tubular shaft (10) is limited to avoid contact of the tubular shaft (10) with the inner wall of said sinus (52).

FIGURE LEGENDS

FIG. 1 shows a standard catheter of the prior art and its placement in a lumen of a vessel, the vessel shown in longitudinal cross-section.

FIG. 2 shows a thin flexible catheter of the prior art and its placement in a lumen of a vessel, the vessel shown in longitudinal cross-section.

FIGS. 15A to 15D show alternative configurations of a catheter for insertion into a dural venous sinus, depending on the placement of the stop member relative to the cranium.

FIGS. 16A to 16C show configurations of a catheter having alternative tubular shafts proximal to the stop member.

DETAILED DESCRIPTION OF THE INVENTION

Figure 3:
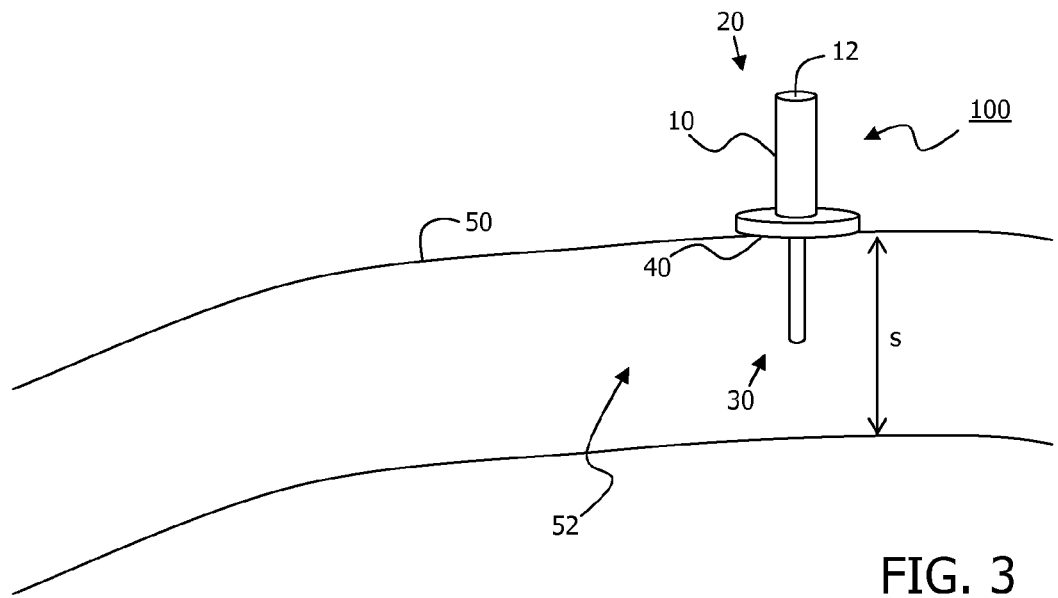
FIG. 3 shows a perspective view of a present catheter and its placement in the lumen of a vessel, the vessel shown in longitudinal cross-section.

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

The terms "distal", "distal end", "proximal" and "proximal end" are used throughout the specification, and are terms generally understood in the field to mean towards (proximal) or away (distal) from the surgeon side of the apparatus. Thus, "proximal (end)" means towards the surgeon side and, therefore, away from the patient side. Conversely, "distal (end)" means towards the patient side and, therefore, away from the surgeon side. Specific to the implantable catheter according to the present invention, the "proximal (end)" means the side where the fluid flow enters the catheter. Conversely, "distal (end)" of an implantable catheter according to the invention means the side where the fluid flow exits the catheter.

With reference to FIG. 3 the present invention concerns a catheter 100, having a proximal 20 end and distal 30 end, for insertion through the outer wall 50 of a bodily lumen 52. The catheter 100 comprises a tubular shaft 10 provided for insertion through the wall 50 of the bodily lumen. The shaft 10 is disposed with a shaft lumen 12. The catheter further comprises a stop element 40. The stop element 40 limits the depth of insertion of the tubular shaft 10 into the bodily lumen 52. The stop element may limit displacement of the tubular shaft into the bodily lumen in transverse direction, i.e. in a direction perpendicular to the longitudinal axis of the bodily lumen taken from the point of insertion of the tubular shaft into the bodily lumen.

The stop element 40 may incorporate a fixation element provided to fix the position of the tubular shaft 10 relative to the point of insertion into the vessel wall. The position may be fixed longitudinally and/or rotationally and/or pivotingly. 50. The fixation element may limit displacement of the tubular shaft in a longitudinal direction, i.e. a direction along the longitudinal axis of the bodily lumen, or rotational direction taken from the point of insertion of the tubular shaft into the bodily lumen. The fixation element may for instance limit rotational, longitudinal or transverse movement of the tubular shaft with respect to the point of insertion or any combination of those. The fixation element is preferably positioned in the epidural layer and thus, the distal tip of the tubular shaft remains in a stable position in the vessel's lumen, unaffected by the thickening of the skull which occurs with age.

The stop element 40 limits the insertion depth, thereby preventing the distal end of the catheter touching the lumen wall after placement. Accordingly, the tubular shaft 10 distal of the stop element 40 is significantly shorter compared with conventional catheters as shown for instance in FIGS. 1 and 2 which do not have a depth limiter. Moreover, the tubular shaft 10 distal of the stop element 40 may be a rigid or semi-rigid. The tubular shaft 10 distal of the stop element may be made of a flexible material. The tubular shaft 10 distal of the stop element may be made of a flexible material comprising a rigid material incorporated in the wall of the flexible material, for instance in the form of braided coils. Conventional catheters (e.g. FIGS. 1 and 2, 102) are typically flexible to facilitate passage through the blood vessel, and avoid damage to the internal wall of lumen. They can cause lesions to the lumen wall during advancement, increasing the risk of blooding clotting for instance. They may be deviated by a luminal septum, causing obstruction. The catheter of the present invention is not advanced along the lumen. The stop element 40 prevents advancement through the bodily lumen, and limits the depth of insertion there into. As there is no contact between the catheter's distal end and the lumen inner wall, the tubular shaft 10 distal of the stop element 40 may be a rigid or semi-rigid, which stiffness maintains the integrity of shape of the shaft lumen 12, contrary to catheters disposed with a flexible shaft.

A standard catheter is disposed with a flexible tip Such flexible tip, however, is capable of bending and flexing in the vessel after insertion (see FIG. 2). The use of a standard catheter with a rigid tip is undesirable as it would scar the vessel upon advancement, and after placement may cause endothelial laceration 54 and, after time, even rupture (see FIG. 1). The present invention precisely places the catheter tip essentially in the centre of the vessel lumen (see FIG. 3), which placement is desirable in many circumstances. The stop element 40 prevents contact of the tip with the vessel wall, thereby reducing or preventing the risk of thrombosis. It is not advanced along a vessel, therefore it may be made from a rigid or semi-rigid material to maintain its position in the vessel even under the force of fluid in the vessel acting on the catheter.

Advantageously, placement of the catheter requires only a puncture of the bodily lumen wall, and insertion into the span of the bodily lumen. Whereas conventional catheters are advanced through the bodily lumen (e.g. venous vessel) by maintaining the catheter essentially parallel with the vessel (see FIGS. 1 and 2), the instant catheter avoids the requirement for clearance around the point of entry, being inserted essentially perpendicular to the lumen outer wall. As such, it is suited where access to the outer wall of the lumen is restricted, for example, to dural venous sinus.

More in particular, the invention provides a catheter that may be integrated into a cerebrospinal fluid shunt system for the evacuation of cerebrospinal fluid from a subject, for instance into a ventriculo-sinus fluid shunt system. A fluid connection (a cerebrospinal fluid shunt) between the ventricles or cisterns of the brain and a dural venous sinus (e.g. superior sagittal sinus, transverse sinus, sigmoid sinus) may be used to treat medical conditions or illnesses in which evacuation of cerebrospinal fluid is dysfunctional. The catheter advantageously avoids the requirement for creating a large opening in the skull, since it can be inserted by essentially perpendicular advancement through the outer wall of the dural venous sinus; as such it requires only a narrow burr hole through the cranium. Moreover, lesion to the wall of the sinus is avoided by circumventing advancement.

The tubular shaft 10 has a proximal 20 and distal 30 end provided for insertion through the wall 50 of the bodily lumen. It is provided with a lumen 12 that extends from the proximal end of the shaft 10 to the distal end.

The shaft lumen 12 is open at the proximal 20 end and contains an opening at distal 30 ends. In other words, the shaft lumen 12 is in fluid connection with a proximal port (orifice) 14 at the proximal end of the shaft 10 and is in fluid connection with a distal port (orifice) 16 at the distal end of the shaft 10. The proximal port may be the proximal terminal end of the shaft. The distal port 16 may be at the distal terminal end of the shaft 10.

Figure 5:
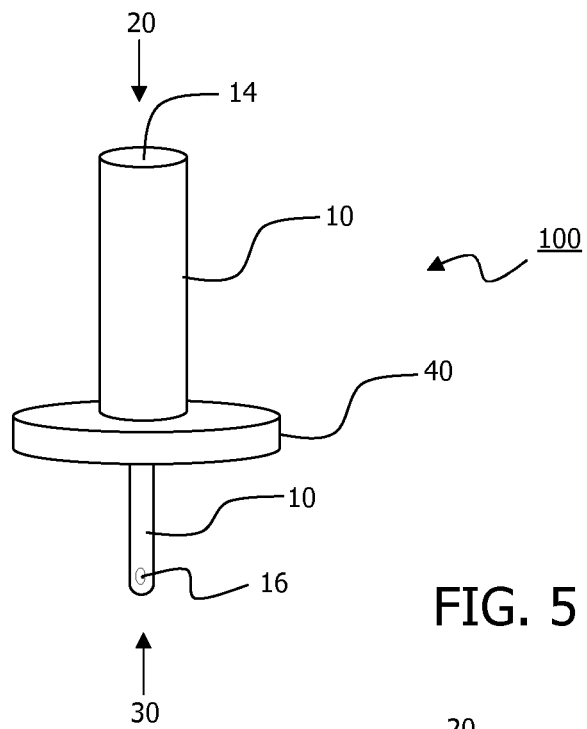
FIG. 5 shows a perspective view of a present catheter where the distal port is disposed at the side.
Figure 7:
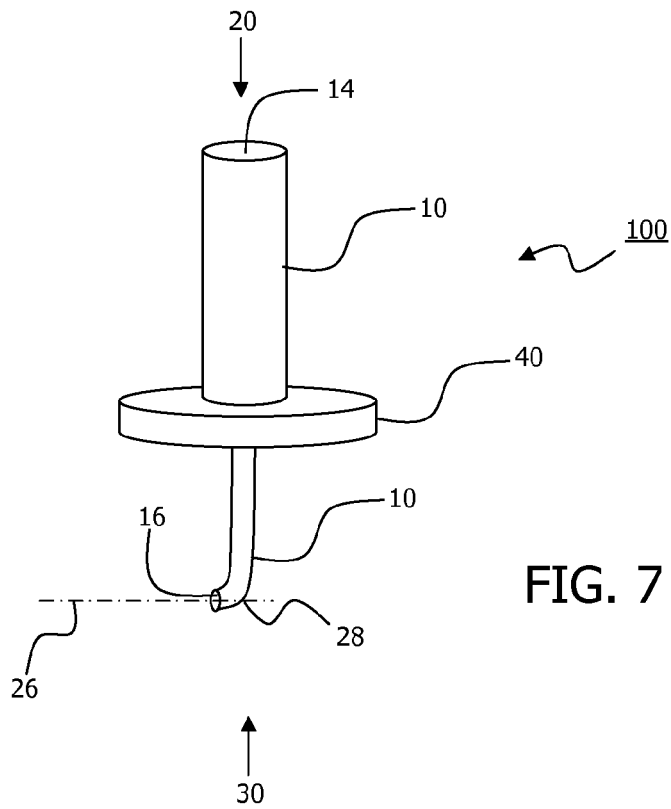
FIG. 7 shows a perspective view of a present catheter where the distal port is orientated such that an imaginary line drawn through the central axis of the distal port touches the inner surface of the tubular shaft 10 distal of the stop element.
Figure 11:
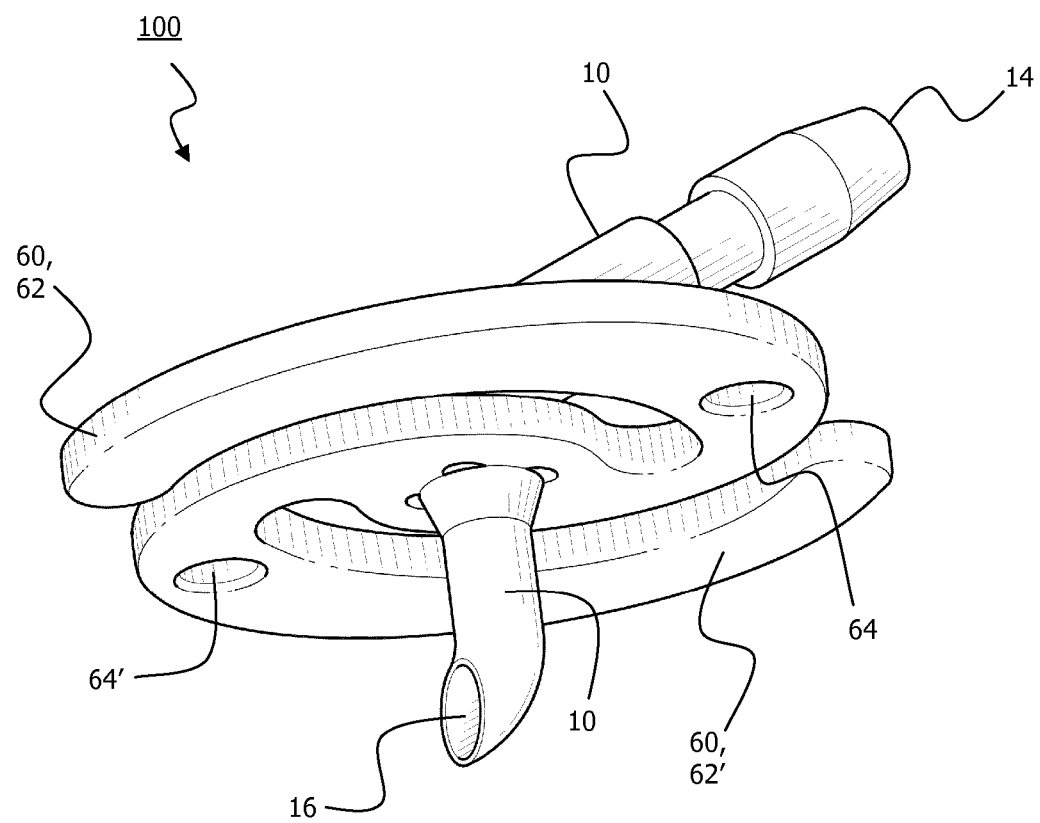
FIG. 11 shows a perspective view of a present catheter where the stop element incorporates fixation elements that are expandable wings.

The distal port is preferably orientated such that it faces the direction of fluid flow in the bodily lumen 52. In particular, when the bodily lumen is a venous vessel. This may be achieved when the distal port 16 is provided to one side of the tubular shaft 10. The distal port 16 may be provided as a side port on the tubular shaft as depicted, for instance, in FIG. 5. The side-port is provided on the body of the shaft 10. Such side-port may not be disposed at the distal terminal end of the tubular shaft 10; the distal terminal end of the tubular shaft may be sealed. The tubular shaft 10 may have an L-shape distal of the stop element 40, as shown for example, in FIGS. 7 and 11. There is preferably one distal port 16.

Figure 6:
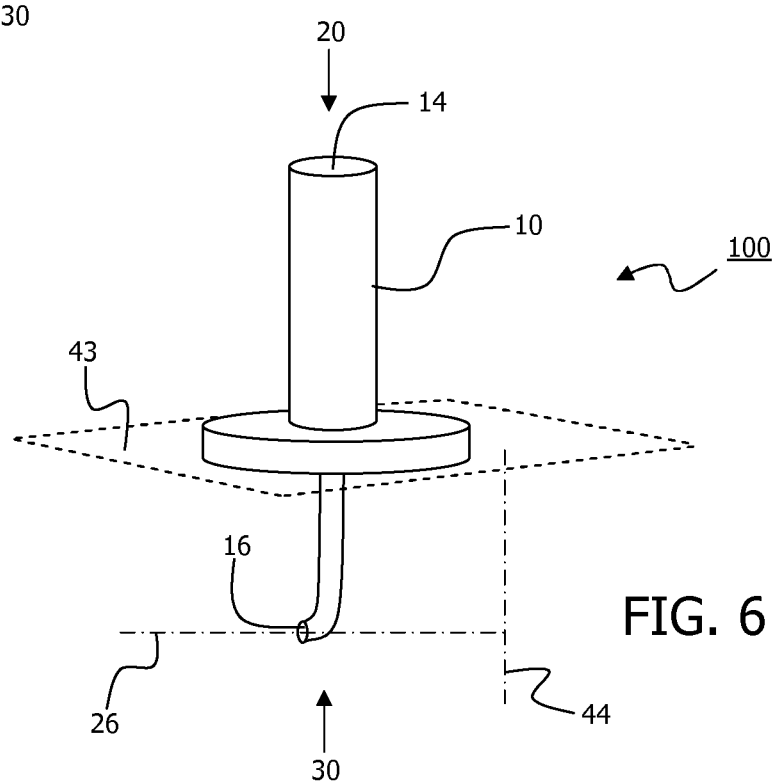
FIG. 6 shows a perspective view of a present catheter where a central axis of the distal port is disposed non-parallel to an axis perpendicular to an imaginary plane that touches maximally a lumen-wall-engaging (distal) surface of the stop element.
Figure 8:
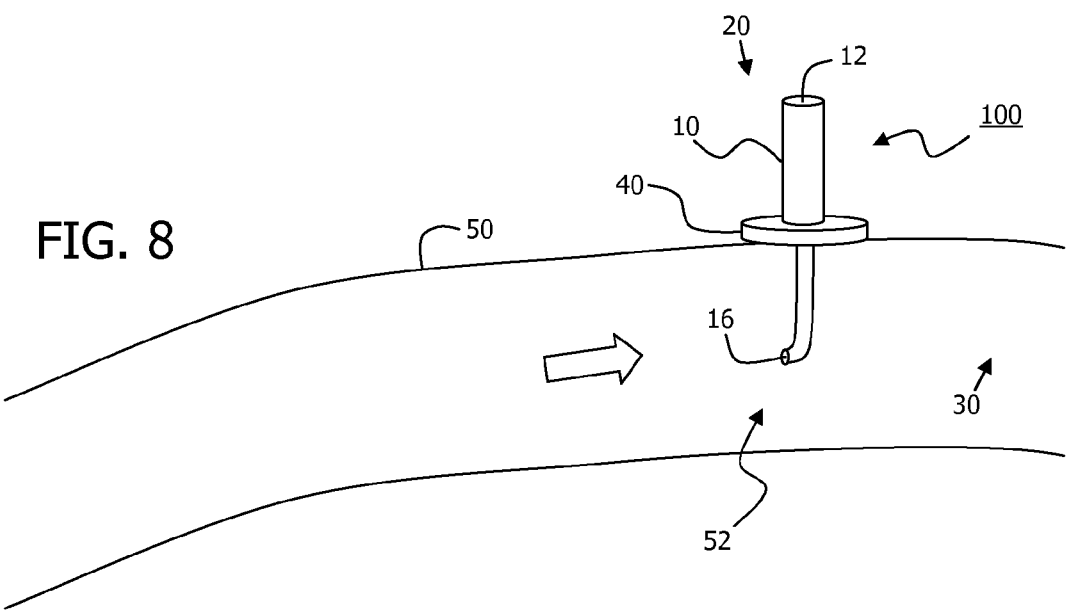
FIG. 8 shows a perspective view of a present catheter its placement in the lumen of a vessel, where the distal port has a retrograde configuration.

The central axis of the distal port 16 may be disposed divergent from or non-parallel to an axis perpendicular to an imaginary plane that touches maximally a lumen-wall-engaging (distal) surface of the stop element 40. In FIG. 6, the imaginary plane 43 is shown together with an axis 44 perpendicular to said imaginary plane 43. The central axis 26 of the distal port 16 is non-parallel to the perpendicular axis 44. It is also within the scope of the invention that the central axis of the distal port 16 is disposed parallel to an axis perpendicular to an imaginary plane that touches maximally a lumen-wall-engaging (distal) surface of the stop element 40. The distal port 16 may be orientated such that an imaginary line 26 drawn through the central axis of the distal port 16 touches 28 the inner surface of the tubular shaft 10 distal of the stop element, as shown for instance, in FIG. 7. The distal port 16 may be orientated to face the direction of flow in the vessel lumen 52 (retrograde). In the retrograde configuration, the distal port 16 points in an upstream direction when the direction of flow is from an upstream to a downstream location. The retrograde configuration is depicted in FIG. 8. The distal port 16 may be orientated to face away from the direction of flow in the vessel lumen 52 (antegrade). In the antegrade configuration, the distal port 16 points in a downstream direction when the direction of flow is from an upstream to a downstream location. The distal port 16 may be orientated parallel to the direction of flow in the vessel lumen 52.

When the catheter 100 is incorporated into a CSF shunt the retrograde orientation is preferred as the distal port 16 will receive the impaction effect created by the velocity of the blood flow inside the dural venous sinus.

The tubular shaft 10 may be linear, however, other shapes are envisaged, include curved, and bent. Where tubular shaft 10 contains a bend, the bend may be curved or angular. The number of bends may be 1, 2, 3, 4, 5 or more. Where a bend is present, it may be in the vicinity or position of the stop element 40. A bend may be in the tubular shaft 10 distal to the stop element 40. A bend may be in the tubular shaft 10 proximal to the stop element 40. Exemplary, non-limiting configurations of different tubular shafts 10 are illustrated in FIGS. 16A to 16C. In FIG. 16A, the tubular shaft is linear from the proximal to distal end. In FIG. 16B, the tubular shaft 10' proximal to the stop element 40 contains a bend. In FIG. 16C, the tubular shaft 10' proximal to the stop element 40 is angled relative to the stop member.

Tubular shaft 10 may have an essentially uniform cross-sectional outer shape (outer profile) from the proximal end 20 to the distal end 30. The tubular shaft 10 may have a non-uniform profile from the proximal end 20 to the distal end 30. The tubular shaft 10 may have a first outer profile distal 30 of the stop element 40, and a second (different) outer profile proximal 20 of the stop element 40. The outer profile may be any, for instance, circular, oval, cam, teardrop, regular polygonal (triangular, oblong (rectangular, square), pentagonal, hexagonal) or irregular polygonal. Preferably it is circular or teardrop.

Tubular shaft 10 may be formed from a single piece of tubing of the same material from the proximal end 20 to the distal end 30. The tubular shaft 10 may be formed from two or more pieces of tubing of different material. The tubular shaft 10 may be formed from tubing of one material distal 30 of the stop element 40, and from tubing of another (different) material proximal 20 of the stop element 40.

The tubing in question may be formed using any suitable process such as an extrusion process or non-extrusion process. It may be formed by micromachining, microinjection molding or dipping. The tubing is preferably formed from a biocompatible material which provides the requisite stiffness. Suitable biocompatible materials include, but are not limited to silicone, a polymer such as polypropylene, polyethylene, polyurethane, polyamide, polyimide, poly(ethylene terephthalate) (PET) or polyesters and copolymers thereof, metal (stainless steel, nitinol) or a combination of metal and polymer, metal and silicone or polymer and silicone. In a preferred embodiment it is formed from a polymeric material that is polyamide or polyimide. In a more preferred embodiment, it is formed from stainless steel or nitinol or a combination or blend of these. In a most preferred embodiment, it is formed from silicone or polyurethane. The tubing may be formed from a shape memory material, such as a shape memory metal, such as for instance nitinol.

An additional electro-polishing may be performed after tubing, hereby reducing friction of the catheter inside the bodily lumens blood stream. Electro-polishing may be performed with a suitable acid/electrolyte solution and a stable potential difference, realized realised for instance by a potentiostat.

The exterior may be coated. The coating may be antithrombotic, hydrophilic, friction reducing or a combination of these. The antithrombotic coating reduces or prevents thrombosis; an example includes heparin. The hydrophilic coating assists the flow of fluid around the tubular shaft 10. Examples includes hyaluronic acid or phosphorylcholine The friction reducing coating reduces friction during insertion, or withdrawal, and/or assists the flow of fluid around the tubular shaft 10. Example of a suitable friction-reducing coating includes Teflon.

Tubular shaft 10 may have an essentially uniform stiffness from the proximal end 20 to the distal end 30. The tubular shaft 10 may have a non-uniform stiffness from the proximal end 20 to the distal end 30. The tubular shaft 10 may have a first stiffness distal 30 of the stop element 40, and a second (different) stiffness proximal 20 of the stop element 40.

The second stiffness may be greater than the first stiffness. The first stiffness may be greater than the second stiffness.

The tubular shaft 10 distal of the stop element is preferably flexurally rigid. The tubular shaft 10 distal of the stop element is preferably flexurally rigid to the extent that it is essentially rigid to the fluid flow in the bodily lumen. In other words, it remains essentially inflexible to the forces applied to its surface by the dynamic flow of fluid in the bodily lumen. The tubular shaft 10 distal of the stop element 40, more in particular, the distal tip thereof, may be configured to flex by a distance equal to or less than 0.01 mm, 1 mm, 2 mm, 3 mm, 4 mm, 5 mm, 6 mm, 7 mm, or a value in the range between any two of the aforementioned values, preferably by a distance equal to or less than 5 mm in the fluid flow of in the bodily lumen compared with the native state. In the native state, there is no force nor stress applied to the tubular shaft 10 distal of the stop element 40. The skilled person would be able to determine the required stiffness of the tubular shaft based upon parameters such as bodily lumen cross-sectional area, fluid flow rate in the vessel, fluid viscosity and the outer diameter of the tubular shaft.

In a preferred embodiment, the tubular shaft 10 distal of the stop element is preferably flexurally rigid to the extent that the distal tip displaces by a maximum distance equal to or less than of 0.01 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, or 16 mm, or a value in the range between any two of the aforementioned values, preferably by a distance equal to or less than 5 mm. The displacement may be measured by determining the distance moved by the distal tip from an initial position where no fluid flows, to a position of maximum displacement from the initial position when fluid flow is applied.

The displacement may be observed in the fluid flow in the lumen compared with a static (no) fluid flow in the bodily lumen. The skilled person can readily determine such a measurement, for instance using an imaging apparatus, such as venography, computer tomography scan, magnetic resonance scan, ultrasound/Doppler imaging and observing and recording movement of the tubular shaft 10 distal of the stop element.

The displacement may be observed in the fluid flow in a flow tube compared with a static (no) fluid flow in the flow tube. The skilled person can readily determine such a measurement, for instance using a liquid flow apparatus having a flow tube for the flow of liquid, containing a window for observing and recording movement of the tubular shaft 10 distal of the stop element. The flow tube preferably has a diameter of 8 to 10 mm. The liquid typically has a density of human blood (1.04 to 1.06 kg/m3) and is held at a temperature of 36.5 to 37.5 deg C. in the flow tube. In flow, the liquid has a flow rate of 8 to 10 cm/s. Displacement induced by the liquid moving from a static to flowing state may be measured using a two, or three dimensional digital camera, and suitable imaging software. The distal tip of the tubular shaft 10 may be provided with a reflective marking.

It is understood that stiffness will depend on a number of factors regarding the tubular shaft 10 such as material of the wall, internal diameter, outer diameter, wall thickness, length of the tubular shaft 10 distal of the stop element which are balanced to optimize its properties.

Tubular shaft 10 may have an essentially uniform outer width or diameter over its length from the proximal end 20 to the distal end 30. The outer width refers to the maximum distance across the outer profile of the tubular shaft e.g. the outer diameter when the tubular shaft 10 has a circular profile. The tubular shaft 10 may have a non-uniform outer width or diameter from the proximal end 20 to the distal end 30. The tubular shaft 10 may have a first maximum outer width or diameter distal 30 of the stop element 40, and a second (different) maximum outer width or diameter proximal 20 of the stop element 40. Preferably the maximum outer width or diameter of the tubular shaft distal 30 of the stop element 40, is less than the maximum outer width or diameter of the tubular shaft proximal 20 of the stop element 40; this is shown in the drawings.

Figure 4:
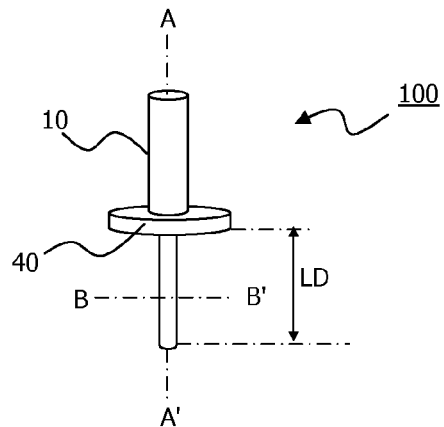
FIG. 4 shows a perspective view of a present catheter with dimensions indicated.
Figure 4A:
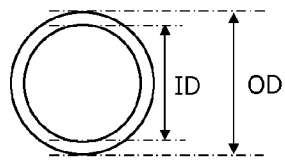
FIG. 4A shows a transverse cross-section of a present catheter across a plane touching line B-B' in FIG. 4.

The maximum outer width or diameter of the tubular shaft 10 will depend on the bodily lumen in question, and factors such as the requisite stiffness. As a general guidance, for insertion into a venous vessel, the maximum outer diameter OD (FIG. 4A) of the tubular shaft 10 distal of the stop element 40 may be equal to or less than 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, or a value in the range between any two of the aforementioned values. Preferably, it is between 0.8 mm and 1.2 mm, most preferably about 1 mm.

Tubular shaft 10 may have an essentially uniform inner diameter from the proximal end 20 to the distal end 30. The tubular shaft 10 may have a non-uniform inner diameter from the proximal end 20 to the distal end 30. The tubular shaft 10 may have a first maximum inner diameter distal 30 of the stop element 40, and a second (different) maximum inner diameter proximal 20 of the stop element 40.

The inner diameter of the tubular shaft 10 will also depend on the bodily lumen in question, and factors such as the requisite stiffness. As a general guidance, for insertion into a venous vessel, the maximum inner diameter ID (FIG. 4A) of the tubular shaft 10 distal of the stop element 40 may be equal to or less than 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, or a value in the range between any two of the aforementioned values. Preferably, it is between 0.7 mm and 1.2 mm, most preferably between 0.7 and 0.8 mm.

The length of the tubular shaft 10 will also depend on the bodily lumen in question, and factors such as the requisite stiffness. The tubular shaft 10 is dimensioned to avoid contact with the inner wall of the bodily lumen 52, more specifically, to avoid contact between the distal end of the tubular shaft 10 and the inner wall of the bodily lumen 52. As a general guidance, for insertion into a venous vessel, the length LD (FIG. 4) of the tubular shaft 10 distal of the stop element 40 may be equal to or less than 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.5 mm, 3 mm, 3.5 mm, 4 mm, 4.5 mm, 5 mm, 5.5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm or a value in the range between any two of the aforementioned values. It may be between 2 mm and 5 mm, or about 4 mm. Preferably, it is equal to or less than 15 mm, or between 3 mm and 11 mm.

Figure 4B:
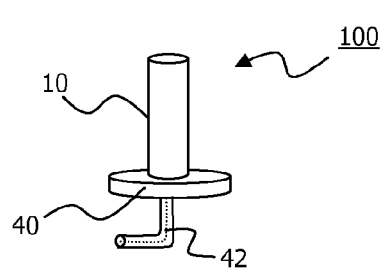
FIGS. 4B to 4C show a perspective view of a present catheter, with various dimension indicators marked.

The length LD may refer to the axial length. The axial length is length of the tubular shaft 10 along its central axis distal of the stop element 40. The length LD may refer to the total length of tubular shaft 10 distal of the stop element 40 including any bends. For instance, the length LD where the tubular shaft 10 contains a bend may be measured along line 42 in FIG. 4B. Preferably, the total length of tubular shaft 10 distal of the stop element 40 is equal to or less than 15 mm, or between 3 mm and 11 mm when the vessel is a dural venous sinus.

Figure 4C:
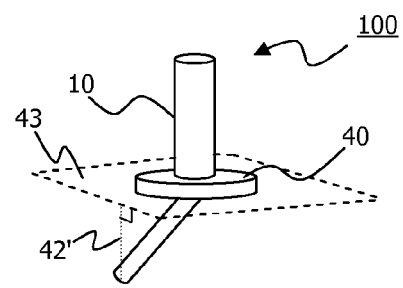

Alternatively, the length LD may refer to the drop length. The drop length is the linear distance from an imaginary plane that touches maximally the engaging surface of the stop element 40 to the distal end (preferably distal terminal end) of the tubular shaft 10, measured along an axis perpendicular to said imaginary plane. FIG. 4C depicts the imaginary plane 43, the perpendicular axis 42' along which the measurement is made to the distal end of the tubular shaft 10. The drop length may be the length of the tubular shaft distal from the point of insertion taken along a transverse direction. The LD may refer to the drop length when the tubular shaft 10 distal of the stop element 40 is angled or bent or not straight. Preferably, the drop length is equal to or less than 9 mm, or between 3 mm and 9 mm when the vessel is a dural venous sinus.

Figure 4D:
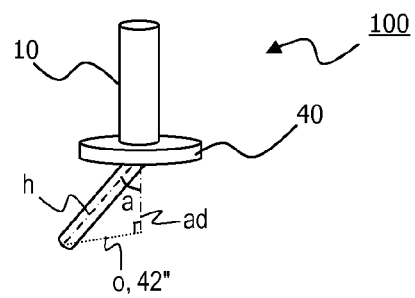
Figure 4E:
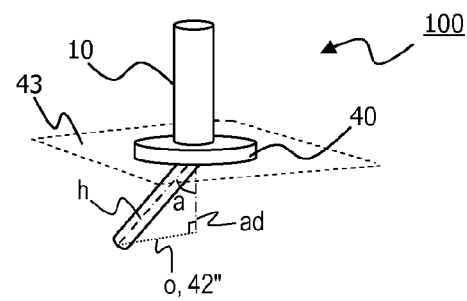

Alternatively, LD may refer to the drop width. The drop width is the length of the opposite side of right angled triangle, having the trigonometrical sides hypotenuse (h), opposite (o) and adjacent (ad), where the opposite side is opposite angle (a). The hypotenuse (h) is the linear distance between distal end (preferably distal terminal end) of the tubular shaft 10 and the point of contact with the stop element, and an angle (a) is the corner of the triangle at said point of contact. FIG. 4D depicts an exemplary right angled triangle having the hypotenuse h, angle a, opposite side o; and adjacent side (ad), where the drop width 42" is measured along the opposite side o of the triangle. In FIG. 4E, the adjacent side (ad) is perpendicular to an imaginary plane 43 that touches maximally the engaging surface of the stop element 40. The drop width may be 0 mm when the tubular shaft 10 distal to the stop element 40 is essentially perpendicular to an imaginary plane that touches maximally the engaging surface of the stop element 40 as shown, for example, in FIG. 5 The drop width may be equal to or less than 1 mm, 2 mm, 3 mm, 4 mm, 5 mm, 6 mm, 7 mm, or 8 mm, or a value in the range between any two of the aforementioned values, preferably between 0 mm and 5 mm, more preferably between 0 mm and 4 mm when the vessel is a dural venous sinus.

In a most preferred embodiment, the tubular shaft distal of the stop element has an outer diameter OD of 1 millimeter and a length of 2 to 5 millimeter thus having a minimal intrasinusal volume (0.5 mm$^2$×π×2 mm or 1.57 mm$^3$ to 0.5 mm$^2$×π×5 mm or 3.925 mm$^3$).

The proximal end of the tubular shaft 10 is preferably provided with a fluidic connector for attachment to a tubing.

A bodily lumen may be present in any natural human or animal bodily structure such as a duct, vascular duct, a bronchial duct, a biliary duct, the oesophasgus, digestive tract, urethral duct, uretheral duct, uterus, stomach, arterial vessel, venous vessel, urethral duct, aeric tract, the urogenital tract, nasopharyngeal area, the pharynx, the small and large bowels, the rectum, the trachea, the uterine cavity, the uterine cervix, the vagina, the urethra, and the bladder or colon. The natural cavity can be any walled cavity of a subject suitable for placing a catheter therein. Preferably it is a venous vessel. More preferably it is a vein disposed in a sinus of the dura mater (dural venous sinus), in particular a superior sagittal sinus, a transverse sinus or a sigmoid sinus. The outer wall of the sinus may include the dura mater. A bodily lumen may be present in any resection cavity after surgical removal of a malignant or benign proliferating mass. The resection cavity can be any resection cavity in a subject, such as brain tumour resection cavity, liver tumour resection cavity, kidney tumour resection cavity, bone tumour resection cavity, breast tumour resection cavity, prostate cancer resection cavity, muscle resection cavity after a sarcoma resection, uterine laparoscopic myoma resection cavity, head and neck tumour resection cavities (tongue tumour resection, partial upper maxillar resection, etc), scar cavity of a melanoma resection, scar cavity of a cheloid resection or any resection cavity known to someone skilled in the art. The span of the bodily lumen should be remain constant or should not change after insertion of the instant catheter to the extent that the distal tip is able to contact an inner wall of the lumen.

Figure 3A:
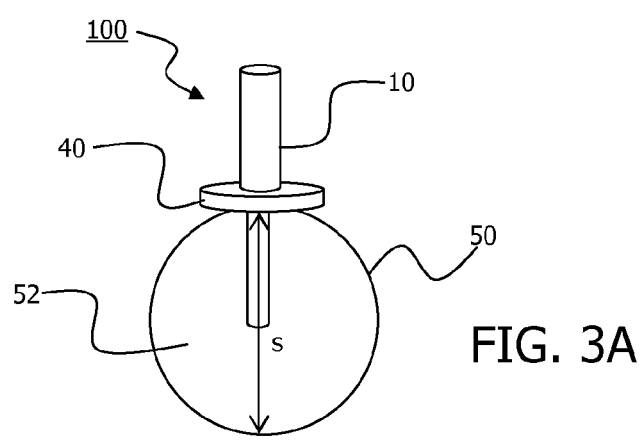
FIG. 3A shows a perspective view of a present catheter its placement in the lumen of a vessel, the vessel shown in longitudinal cross-section.

The bodily lumen preferably maintains an essentially constant transverse cross-sectional shape (inner profile). The span ("s", FIG. 3) of the bodily lumen is the maximum width of the inner profile (see FIG. 3A). It is preferably measured from where the catheter enters the lumen. Otherwise expressed, the span of the bodily lumen is the maximum width of a transverse cross section of the bodily lumen, i.e. a section perpendicular to a longitudinal axis of the bodily lumen, (see FIG. 3A) taken from a point from where the catheter enters the lumen.

For a lumen having a circular inner profile, it is equivalent to the inner diameter. By restricting the depth of insertion of the tubular shaft to a fraction of the span of the lumen, contact between the tubular shaft and lumen wall is avoided. As a consequence, the tubular shaft 10 distal of the stop element may be rigid without risk of damage to the lumen wall. It will be appreciated that the span of a lumen may be measured using an imaging apparatus, such as venography, computer tomography scan, magnetic resonance scan, ultrasound/Doppler imaging. The catheter 100 may be pre-selected or adjusted so that stop element 40 limits the depth of insertion of the tubular shaft to less than the span of the vessel lumen 52.

Where in the bodily lumen is a dural venous sinus, the span is between 3 mm and 10 mm, as is well understood in the art.

The stop element 40 is a distance limiter, that limits the insertion of the tubular shaft 10 into the bodily lumen. It effectively determines the length LD of the tubular shaft 10 distal to the stop element 40. The stop element 40 abuts with the vessel wall or with a structure in stable or fixed relation with the vessel wall which structure may be a skull bone for instance. Preferably, the stop element 40 abuts with the outer wall of the bodily lumen 52. It enables the practitioner to ascertain when the correct insertion depth is reached.

The insertion depth is the protruding length of tubular shaft 10 within the lumen 52. The insertion depth may refer to the protruding length of the tubular shaft 10 within the lumen 52 measured along a line between the distal end of the shaft 10 and an imaginary plane that maximally contacts the engaging surface of the stop element 40, which line is perpendicular to the plane.

The depth of insertion of the tubular shaft 10 may be limited to less than the span "s" (FIGS. 3, 3A) of the bodily lumen 52, which is measured in transverse cross-section. The depth of insertion of the tubular shaft 10 may be limited to 10%, 20%, 30%, 40%, 50%, 60%, 70%, 80%, preferably between 40% and 60% less than the span "s" of the bodily lumen 52. It will be appreciated that the length LD of the tubular shaft 10 distal of the stop element 40 will be adjusted to provide the correct depth of insertion, accounting for the thickness of the bodily lumen wall.

The stop element 40 may take the form of any distance-limiting stop mechanism. For instance, an annular collar, one or a plurality of protrusions arranged circumferentially around the outer surface of the tubular shaft 10. It may take the form of one or more bends in the shape of the tubular shaft 10. It may take the form of an interface between two different outer diameters of the tubular shaft 10; the interface may be abrupt and not gradual. The outer profile of the stop element 40 is larger than that of the tubular shaft 10. It is understood to be larger than the incision in the wall of the bodily lumen into which the tubular shaft 10 is placed.

The stop element 40 may be rigidly attached to the tubular shaft 10. The rigid attachment may be to the extent that displacement and/or rotation relative to the tubular shaft 10 is prevented. The stop element 40 may be slidably mounted onto the tubular shaft 10; a locking mechanism may be provided to lock displacement of the stop element 40 relative to the tubular shaft 10 at the correct position. The stop element 40 may in revolute attachment to the tubular shaft 10; a locking mechanism may be provided to lock rotation stop element 40 relative to the tubular shaft 10 at the correct position. The stop element 40 is preferably in fixed revolute relation to the tubular shaft 10 at least distal of the stop element 40.

Depth of insertion of the tubular shaft into the bodily lumen may be measured as the depth of insertion of the tubular shaft in transverse direction, i.e. in a direction perpendicular to a longitudinal axis of the bodily lumen The stop element 40 may incorporate a fixation element 60 configured to fix the position of the tubular shaft 10 relative to the point of insertion into the bodily lumen outer wall 50. The fixation element may take the form of a suture eyelet, hook, adhesive pad, clip, brace, band, or any suitable element for affixing the stop element 40 to the bodily lumen outer wall 50. The stop element 40 may require no or minimal adaptation to incorporate a fixation element 60. The fixation element 60 may have the same functionality as the stop element 40, or vice versa. This is the case where the fixation element is comprised in expandable wings (see below). The fixation element 60 may maintain the tubular shaft 10 distal to the stop element 40 in fixed revolute relation with the point of insertion.

The stop element and/or the fixation element may be positioned in the epidural space between the dural layer and the internal cortical layer of the skull bone. In other words, stop element and/or the fixation element may be configured for epidural placement. Advantageously, epidural placement avoids the problem of fixation to the bone in cases where the cranium is subject to movement relative to the dural venous sinus, for instance, during growth and development when the bone of the skull (e.g. in infants). In particular, children may exhibit a displacement of 2 mm to 15 mm which would cause the catheter to retract from the sinus.

In a preferred embodiment, the stop element 40 comprises one or more wings that are fixation elements 60. The wings may be expandable wings 62, 62', as shown for instance, in FIGS. 9, 10 and 11. The wings may be fixed (of fixed span, non-expandable) wings 65, 65' with respect to the tubular shaft, as shown for instance, in FIG. 14. The number of wings may be 2, 3, 4 or more, most preferably 2. The wings are preferably evenly distributed around the periphery of the circumference of the tubular shaft 10. When there are two wings, they are preferably diametrically opposed around the central axis of the tubular shaft 10. It is noted that the wings provide the functionality of the stop element 40. The wings 62, 62' fix the tubular shaft 10 in position where a compressible gap exists between two structures such as between two membranes. Such gap exists between the cranium and the dura mater, for example, in which case the fixation element 60 and/or stop element 40 are configured for epidural attachment. A wing is preferably flat or planar.

A wing preferably has a limited thickness to allow fixation, in particular epidural placement. A wing may have a maximum thickness equal to or less than 0.02 mm, 0.04 mm, 0.06 mm, 0.08 mm, 0.1 mm, 0.12 mm, 0.15 mm, 0.2 mm, 0.25 mm, 0.5 mm, 0.75 mm, 1 mm, 1.2 mm, 1.4 mm, 1.5 mm, 1.6 mm, 1.8 mm, 2 mm. For an expandable wing, the thickness is preferably between 0.1 and 1.5 mm, most preferably around 0.5 mm. For a non-expandable wing, the maximum thickness may be less than 2 mm, more preferably less than 1 mm.

Preferably a planar surface of a wing 62, 62' is disposed perpendicular to an axis parallel to the central axis of the tubular shaft 10 where it attaches to the tubular shaft 10.

An expandable wing 62, 62' is preferably flat and expands in a planar direction i.e. perpendicular to an axis parallel to the central axis of the tubular shaft 10 where it attaches to the tubular shaft 10. During expansion, the thickness of the wing is preferably essentially constant.

Figure 9:
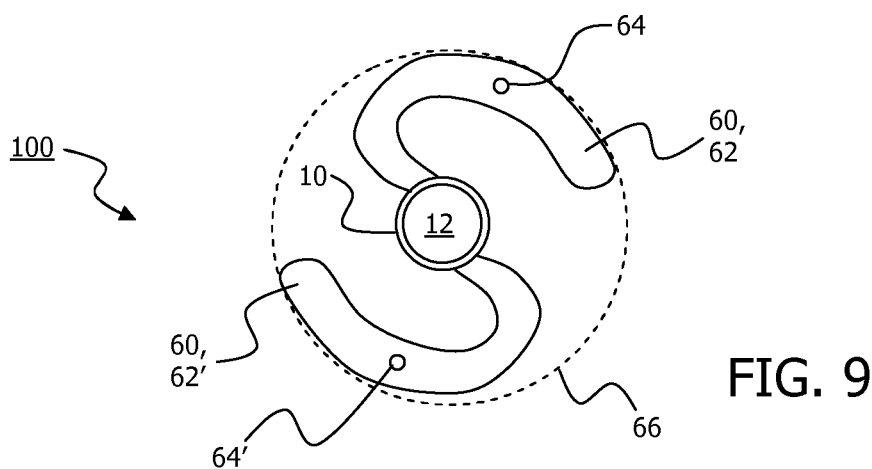
FIG. 9 shows a plan view of a present catheter where the stop element incorporates fixation elements that are expandable wings which are closed.
Figure 10:
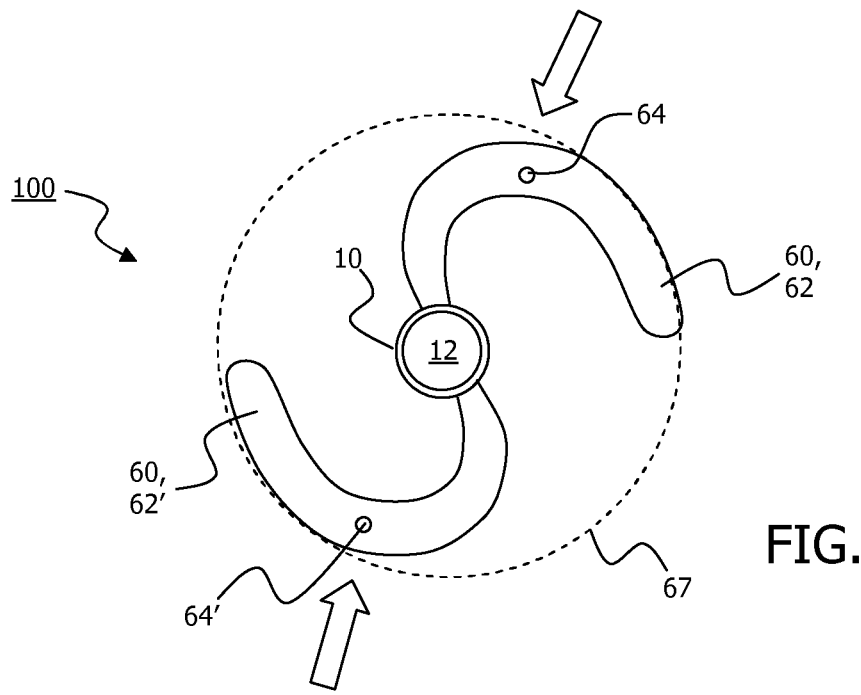
FIG. 10 shows a plan view of a present catheter where the stop element incorporates fixation elements that are expandable wings which are open.

There may be two extremities of movement by the wing—a closed position as illustrated in FIG. 9 where the wings 62, 62' are "folded" and the fixation element 60, 60' has a smaller outer profile bound by a fictive circle 66 centred on the central axis of the tubular shaft, and an open position as illustrated in FIG. 10 where the wings 62, 62' are "unfolded" and the fixation element 60 has a larger outer profile bound by a larger fictive circle 67. In particular, attachment is facilitated when access to the point of attachment is through a burr hole in one of the structures accessed by folding the wings.

The difference in diameter or span of the expandable fixation element 60 between its closed and open positions will be determined by the skilled artisan, depending on the point of insertion and access, among other factors. When it is to be used as a CSF shunt, the span may be equal to or less than 2 mm, 3 mm, 4 mm, 5 mm, 6 mm, 7 mm, 8 mm, 9 mm, 10 mm, or a value in the range between any two of the aforementioned values, preferably between 8 mm and 10 mm in the closed position. When it is to be used as a CSF shunt, the span may be equal to or less than 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or a value in the range between any two of the aforementioned values, preferably between 13 mm and 20 mm in the open position.

Movement between the open and closed position may be mechanically actuated. In other words, a radial force applied to the wings 62, 62' directs them into the requisite position. For instance, a pliers-like tool disposed with pointed jaws may dismountably engage with a notch 64, 64' on each wing 62, 62', so that the wings can be radially expanded or contracted responsive to movement of the pliers jaws. In a preferred aspect, the wings 62, 62' are springs that maintain an open position and elastically deform (are compressed) into the closed position. Advantageously, the winged fixation element 60 can be inserted and removed repeatedly. Since fixation relies on frictional contact between structures, it is essentially atraumatic. As the closed span of the fixation element 60 is relatively small, it is apt for use in key-hole surgery with minimal invasiveness.

A non-expandable wing 65, 65' has a fixed span. It is preferably flat or planar. It is preferably longitudinal. It may have an outer profile that is a longitudinal petal, or oval. In plan view—viewed along the central axis of the tubular shaft—a non-expandable wing 65, 65' provides the fixation element having a longitudinal shape. Where there are two non-expandable wings, the plan view preferably is propeller-like. Prior to insertion, and for epidural fixation, an oval or slot-shaped burr hole is prepared in the cranium having a shape that receives the fixation element. Having operatively inserted the catheter, such that the wings of aligned within the slot, the position of the catheter may be fixed by rotation of the shaft, which brings the wings out of alignment with the slot. Rotation may be between 30 and 150 deg, preferably 90 degrees when there are two wings diametrically opposed.

Accordingly, the wings are placed epidurally and beneath the cranium, which serve to fix the position of the catheter. It is preferred that the fixation element 60 is provided with two non-expandable wing 65, 65' diametrically opposed around the central axis of the tubular shaft 10.

Figure 14:
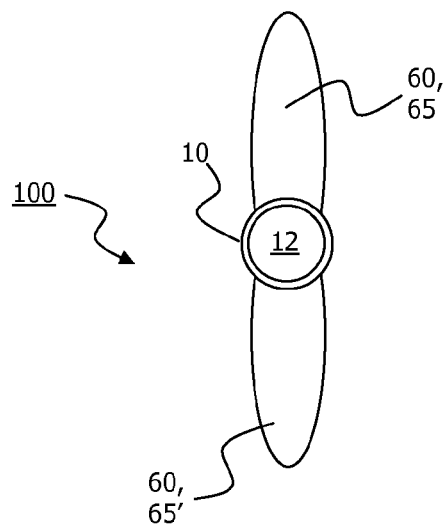
FIG. 14 shows a plan view of a present catheter where the stop element incorporates fixation elements that are non-expandable wings.
Figure 14A:
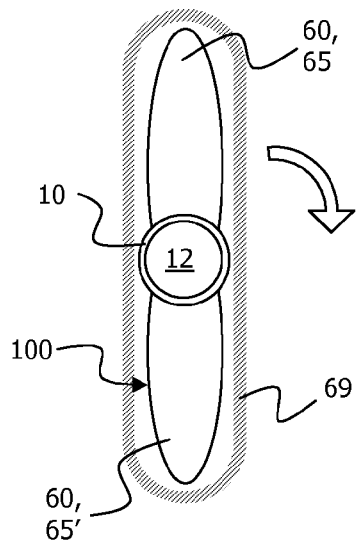
FIG. 14A shows a catheter of FIG. 14 disposed in a slot-like burr hole in the cranium.
Figure 14B:
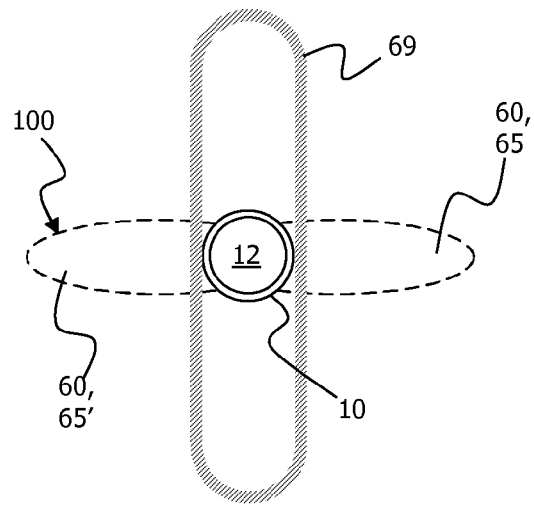
FIG. 14B shows the catheter of FIG. 14A rotated around the central axis of the tubular shaft by 90 deg, and locked into position.

In FIG. 14, is a plan view of a catheter 100 provided with fixation element 60 comprising a pair of non-expandable wing 65, 65' arranged diametrically around the central axis of the tubular shaft 10. FIG. 14A, the catheter 100 is disposed in a slot-like burr hole 69 in the cranium of a subject. FIG. 14B, the catheter 100 has been rotated 90 deg, such that the non-expandable wing 65, 65' enter the epidural space, and are motion-limited by the cranium.

A planar wing may be constructed from one or more suitable materials having the requisite biocompatible properties. Where the wing is a spring, it will be compressible (elastically deformable). Suitable materials include a polymer such as polypropylene, polyethylene, polyurethanes, polyurethane, polyamide, polyimide poly(ethylene terephthalate) (PET) or polyesters and copolymers thereof, metal (stainless steel, nitinol) or a combination of metal and polymer, metal and silicone or popolymer and silicone. In a preferred embodiment it is formed from a polymeric material that is polyamide or polyimide. In a more preferred embodiment, it is formed from stainless steel or nitinol or a combination or blend of these. In a most preferred embodiment, it is formed from stainless steel or nitinol or a combination or blend of these. In a most preferred embodiment, it is formed from nitinol or polyurethane.

The fixation element 60 comprising wings 62, 62' may be prepared using a pattern of cuts in a sheet of suitable material such as nitinol or stainless steel. A standard technique for the manufacture of a fixation element 60 is laser cutting technology which can produce the fixation element 60 in an automatic manner e.g. by computer numeric controlled (CNC) cutting. Adjustments to the cutting due to sizes of wing or pattern of cuts can be automatically computed and modified cutting regimes implemented. Other methods may also be suitable, including water jet cutting, electrochemical etching, electrical discharge machining, diamond cutting, simple knife cutting, or any other suitable technique preferably followed by a suitable surface treatment, like etching or electropolishing to deburr and or round off possible sharp edges. Alternatively, a fixation element 60 comprising wings 62, 62' may be formed by micro-molding for instance when they are made from polymer.

FIGS. 15 A to 15D illustrate exemplary non-limiting configurations of the catheter in situ. In FIG. 15A, the catheter is implanted such that the stop element 40 (and fixation element 60) is disposed in the epidural space 76 between the dural layer 78 and the internal cortical layer of the skill bone 74 the tabula interna. In FIG. 15B, a hole is provided though the skull bone 74 that is flanked by an annular ring portion that is disposed partially through the depth of the skull bone 74. The stop element (and fixation element 60) of the catheter engages with the annular ring portion to limit the insertion depth of the tubular shaft. In FIG. 15C, the stop element 40 (and fixation element 60) is disposed on the outer side of the skill bone 74. In FIG. 15D, the stop element 40 (and fixation element 60) is formed by virtue of a surface at an interface between two different diameters of the tubular shaft 10; a hole is provided though the skull bone 74 that is flanked by an annular ring portion that is disposed partially through the depth of the skull bone 74. The stop element at the interface engages with the annular ring portion to limit the insertion depth of the tubular shaft.

In particular, the catheter 100 may be incorporated into a cerebrospinal fluid (CSF) shunt system for the evacuation of cerebrospinal fluid from a subject into a sinus of the dura mater. In particular a CSF shunt may be a ventriculosinus shunt, most preferably a retrograde ventriculo-sagittal sinus shunt. The catheter 100 may be part of the sinus end of a ventriculosinus CSF shunt. A CSF shunt may be realized by joining via tubing 45, or extending the tubular shaft 10 proximal of the stop element 40 to a ventricular drainage catheter 43. A flow valve, preferably a one way flow valve 47 may optionally provided inline with the tubing 45, although this may not be a requirement for functioning of the shunt. According to one aspect, the CSF shunt is devoid of a flow valve.

Figure 12:
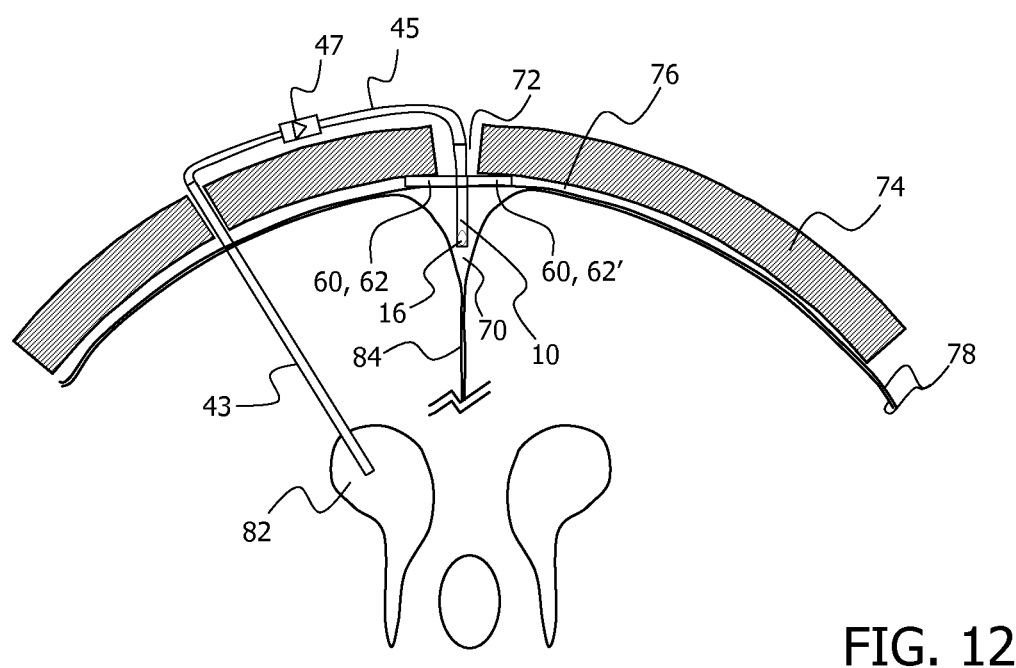
FIG. 12 shows a catheter of the present invention incorporated into a CSF shunt, implanted in situ.

A cerebrospinal fluid shunt (CSF) system is illustrated, for instance, in FIG. 12. The stop member incorporating a fixation element 60, which comprises a pair of sprung wings 62, 62', abuts the outside surface of the wall of dural venous sinus 70 and can be positioned in the epidural space 76, between the dural layer 78 and the internal cortical layer of the skull bone 74, the tabula interna. Also illustrated is the felix cerebri 84. The catheter 100 is introduced through a small burr hole 72 in the skull; the wings 62, 62' will be compressed or 'closed'. A suitable tool may grip the catheter, and at the same time, compress the wings 62, 62'. The wings 62, 62' act in the closed position as a stop element 40. Once the position distal tip of the tubular shaft 10 and the orientation of the direction of the distal port 16 are satisfactory, the compression of the wings 62, 62' is released and they open spontaneously and secure themselves in the epidural space 76 around the burr hole 72. In effect, a dural suture is obtained around on or both wings.

The tubular shaft 10 distal of the stop element 40 is preferably made of rigid material. Because of its essentially perpendicular introduction and because of the short length of tubular shaft 10 distal of the stop element 40, its distal tip of the tubular shaft 10 cannot cause endothelial wall lesions. Also the risk of a conflict with an intrasinusal septum is reduced to a minimal level. Because of its perpendicular introduction combined with its narrow outer diameter of ideally around 1 millimeter, introducing the catheter 100 only requires a puncture of the superior sinuses wall, minimizing the risk of blood loss and minimizing the risk of aspiration of air inside the venous sinus. The design facilitates an essentially perpendicular introduction angle that precludes the technically cumbersome oblique angle introduction of the catheter. Furthermore, the design of the catheter will not only allow ante- or retrograde orientation of its port, also an orientation of the port parallel to the blood flow is feasible. The stable/fixed position and orientation of the catheter and its design will allow a straightforward and stress free subgaleal trajectory of the shunt's tubing.

Figure 13:
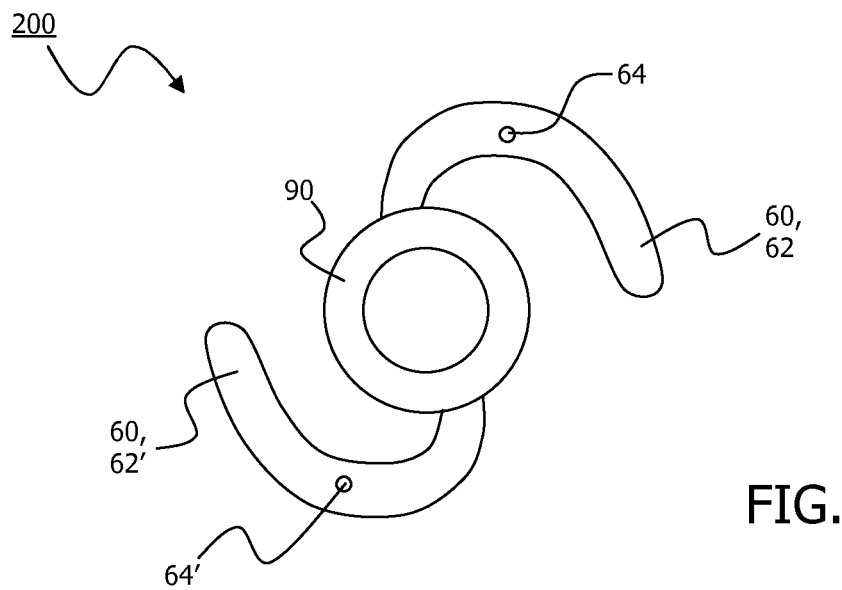
FIG. 13 shows a plan view of a fixation element.
Figure 13A:
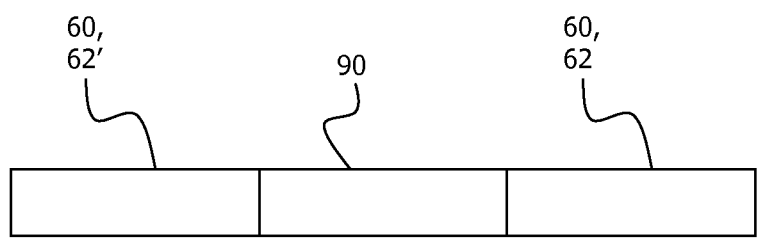
FIG. 13A shows a side view of a fixation element.

One embodiment of the invention provides an expandable support 200 for bodily insertion, comprising a centrally arranged coupling element 90 attached to one or more expandable wings 62, 62', as shown for instance, in FIGS. 13 and 13A. The number of wings may be 2, 3, 4 or more, most preferably 2. The wings 62, 62' are preferably evenly distributed around the periphery of the coupling element 90. The wings fix the coupling element in position where a compressible gap exists between two structures such as between two membranes. Such gap exists between the cranium and the dura mater. In particular, attachment is facilitated when access to the point of attachment is through a burr hole in one of the structures accessed by folding the wings.

The coupling element 90 is configured for attachment to a reciprocating element such as a sensor, a drug-eluting structure (prosthesis), an electrical-stimulation probe, a transducer (transmitter or detector of light, acoustic energy, ultrasonic energy heat). The coupling element 90 may be provided with a cavity 92 into which the reciprocating element fits. Attachment of the reciprocating element to the coupling element 90 may be rigid, permanent, dismountable, revolute. Attachment may be realized by adhesive, welding, frictional attachment, crimping, clamping, screwing or any mean known in the art.

A wing 62, 62' is preferably flat, and expands in a planar direction. During expansion, the thickness of the wing is preferably essentially constant.

There may be two extremities of movement by the wing—a closed position where the wings are "folded" and the fixation element has a smaller outer profile, and an open position where the wings are "unfolded" and the fixation element has a larger outer profile.

Movement between the open and closed position may be mechanically actuated. In other words, a force applied to the wings 62, 62' moves them into the requisite position. For instance, a pliers-like tool disposed with pointed jaws may dismountably engage with a notch 64, 64' on each wing 62, 62', so that the wings can be radially expanded or contracted responsive to movement of the pliers jaws. In a preferred aspect, the wings 62, 62' are springs that maintain an open position and elastically deform (are compressed) into the closed position. Advantageously, the expandable support 200 can be inserted and removed repeatedly. Since fixation relies on frictional contact between structures, it is essentially atraumatic. As the closed span of the expandable support 200 is relatively small, it is apt for use in key-hole surgery with minimal invasiveness.

A planar wing may be constructed from any suitable material having the requisite biocompatible properties. Where the wing is a spring, it will be compressible (elastically deformable). Suitable materials include stainless steel or nitinol or a combination or blend of these.

The expandable support 200 may be prepared using a pattern of cuts in a sheet of suitable material such as nitinol or stainless steel. A standard technique for the manufacture of an expandable support 200 is laser cutting technology which can produce the expandable support 200 in an automatic manner e.g. by computer numeric controlled (CNC) cutting. Adjustments to the cutting due to sizes of wing or pattern of cuts can be automatically computed and modified cutting regimes implemented. Other methods may also be suitable, including water jet cutting, electrochemical etching, electrical discharge machining, diamond cutting, simple knife cutting, or any other suitable technique preferably followed by a suitable surface treatment, like etching or electro-polishing to deburr and or round off possible sharp edges.

The present invention also provides for a method of manufacture of a catheter 100 as described herein. The invention also provides for a use of a catheter 100 as defined herein for the manufacture of a device for insertion through a wall 50 of a sinus of the dura mater in a subject. In particular, the method and use are such that the insertion depth of the tubular shaft 10 is limited to avoid contact of the tubular shaft 10 with the inner wall of said vein. The limitations described in respect of the catheter also apply to the method of manufacture and use. The depth of insertion of the tubular shaft 10 of the catheter may be limited to less than the span of the bodily lumen 52 in transverse cross-section. The depth of insertion of the tubular shaft 10 may be limited to essentially half of the span of the bodily lumen 52. The stop element 40 may incorporate a fixation element 60, configured to fix the position of the tubular shaft 10 relative to the point of insertion into the wall 50 of the bodily lumen 52. The fixation element 60 may comprise one or more wings that may be expandable wings 62, 62' or non-expandable (fixed) wings 65, 65'. Preferably the wings expand in a plane. The expandable wings 62, 62' may be configured to expand in the space between the cranium and the dura mater. The tubular shaft 10 distal to the stop element 40 may be in fixed revolute relation with the point of insertion. The insertion depth of the tubular shaft 10 may be limited to avoid contact of the tubular shaft 10 with the inner wall of the bodily lumen 52. The distal port 16 of the catheter may be oriented to face the direction of flow in the vessel lumen 52. The bodily lumen 52 may a dural venous sinus, in particular in the superior sagittal sinus, transverse sinuses, or sigmoid sinus.

Possible steps for an implantation of the catheter 100 are described. A catheter 100 is provided with a stop element 40 incorporating a fixation element 60 of two compressible wings made of nitinol. The outer profile of the wings in the closed position has a maximum span of 8-10 mm, and the wings are sprung to return to the open position. The outer diameter of the tubular shaft distal of the stop element 40 is 1 mm. The catheter is attached at the proximal end to a ventricular drainage catheter 43 by a tubing disposed with or without a unidirectional valve.

A burr hole 72 is made in the skull bone 74 with a diameter of 8 to 10 millimeter and on top of the center of the dural venous sinus 70. Using medical imaging (e.g. venography, neuronavigation, computer tomography scan, magnetic resonance scan, ultrasound/Doppler imaging) the center of the dural venous sinus 70 and the distance from the outside surface of the upper wall of the dural venous sinus 70 to the center of the dural venous sinus 70 is determined. The position of the stop element 40 is selected accordingly, such that the insertion depth of shaft 10 is equal to or less than the determined distance, preferably less than half of the determined distance. Typically it is 2 to 5 mm. The distal port 16 is provided on the side of the tubular shaft 10, or at the distal tip of the tubular shaft 10.

The catheter 100 is introduced perpendicularly with respect to the upper wall of dural venous sinus 70. The distal port 16 of the tubular shaft 10 is positioned near a position where the blood flow is maximal, for instance near the center of dural venous sinus, at maximal distance of the sinus's internal walls. Maximum blood flow position is for instance determined using Doppler imaging techniques. The distal port 16 is located at one side of the tubular shaft 10; this allows the port to be directed against the direction of the blood flow (retrograde) or in the direction of the blood flow (antegrade). In the retrograde orientation, a maximal impaction effect will be obtained as the distal port 16 will be at the dural venous sinus's center, where the blood flow's velocity is maximal.

The fixation and/or stop element is preferably deployed in the epidural layer, thereby positioning and/or fixing the implantable catheter in the epidural space. Where the fixation element comprises one or more expandable wings 62, 62', the wings are released and they spring open into the epidural space, thereby fixing the catheter. Where the fixation element comprises non-expandable (fixed span) wings 65, 65', they may be fixed into a slot-like burr hole by a rotation along the central axis the distal tube, preferably by 40 to 60 deg.

The proximal port 14 is connected to a ventricle drainage catheter 43 by way of tubing 45 and—if indicated—a unidirectional valve blocking backflow from the dural venous sinus to the brain's ventricle. The ventricle drainage catheter is introduced using a burr hole made in the skull bone 74 with a diameter of 6 to 10 millimeter and in the vicinity of the ventricle. Using medical imaging again (e.g., computer tomography scan, magnetic resonance scan, ultrasound/Doppler imaging, neuronavigation techniques) the position of the ventricle, and the distance from the outside surface of the dura to the center of the ventricle are determined. The ventricle drainage catheter 45 is introduced. The tip of the ventricle drainage catheter 45 is positioned in the center of the ventricle. Once the distal port of the ventricle drainage catheter connected with the proximal port of the tubular shaft (with or without an interposed unidirectional valve), the tubing 26 is disposed in the subgaleal layer.

Some Further Embodiments of the Invention

The present invention relates to a catheter (100) provided for insertion through a wall (50) of a bodily lumen (52), having a proximal (20) and distal end (30), comprising:
- a tubular shaft (10) for insertion through the wall (50) of the bodily lumen into the bodily lumen (52), provided with a shaft lumen (12) in fluid connection with a proximal port (14) at the proximal end and a distal port (16) at the distal end of the shaft (10), and
- a stop element (40) disposed on an outer surface of the tubular shaft (10), configured to limit the depth of insertion of the tubular shaft (10) into the bodily lumen.

The depth of insertion of the tubular shaft (10) of the catheter may be limited to less than the span of the bodily lumen (52) in transverse cross-section.

The depth of insertion of the tubular shaft (10) may be limited to essentially half of the span of the bodily lumen (52). The stop element (40) may incorporate a fixation element (60), configured to fix the position of the tubular shaft (10) relative to the point of insertion into the wall (50) of the bodily lumen (52). The fixation element (60) may comprise one or more expandable wings (62, 62'). Preferably the wings expand in a plane. The wings (62, 62') may be configured to expand in the space between the cranium and the dura mater. The expandable wings (62, 62') may be springs that maintain open wings in an uncompressed state. The stop element (40) may be fixed or slidable in relation to the tubular shaft (10). The tubular shaft (10) distal to the stop element (40) may be in fixed revolute relation with the point of insertion. The tubular shaft (10) may be flexurally rigid to fluid flow in the bodily lumen (52). The insertion depth of the tubular shaft (10) may be limited to avoid contact of the tubular shaft (10) with the inner wall of the bodily lumen (52). The tubular shaft (10), distal of the stop element (40), may have a length of 10 mm or less. The distal port (16) may be provided to one side of the tubular shaft (10). An imaginary line drawn through the central axis of the distal port (16) may touch the inner surface of the tubular shaft (10) distal of the stop element (40). The distal port (16) of the catheter may be oriented to face the direction of flow in the vessel lumen (52).

The invention claimed is:

1. An implantable catheter provided for insertion through a wall of a dural venous sinus in a subject, having a proximal and distal end, comprising:
 - a tubular shaft for insertion through the wall of the venous sinus into the sinus, provided with a shaft lumen in fluid connection with a proximal port at the proximal end and a distal port at the distal end of the shaft;
 - a stop element disposed on an outer surface of the tubular shaft, configured to limit the depth of insertion of the tubular shaft into the sinus; and
 - wherein the drop length of tubular shaft distal to the stop element, that is the linear distance from an imaginary plane that contacts maximally the engaging surface of the stop element to the distal end of the tubular shaft, measured along an axis perpendicular to said imaginary plane, is equal to or less than 9 mm.

2. Catheter according to claim 1, wherein the depth of insertion of the tubular shaft is limited to less than the span of said sinus in transverse cross-section.

3. Catheter according to claim 2, wherein the depth of insertion of the tubular shaft is limited to essentially half of the span of said sinus.

4. Catheter according to claim 1, wherein the stop element incorporates a fixation element, configured to fix the position of the tubular shaft relative to the point of insertion into the wall of said sinus.

5. Catheter according to claim 1, wherein the stop element and/or fixation element is configured for epidural placement.

6. Catheter according to claim 4, wherein the fixation element comprises one or more wings.

7. Catheter according to claim 6, wherein the wings are expandable wings and comprise springs that maintain open wings in an uncompressed state.

8. Catheter according to claim 6, wherein said wings are configured to expand in the space between the cranium and the dura mater.

9. Catheter according to claim 1, wherein the insertion depth of the tubular shaft is limited to avoid contact of the tubular shaft with the inner wall of said sinus.

10. Catheter according to claim 1, wherein the distal port is provided as a side port on the tubular shaft.

11. Catheter according to claim 1, wherein the distal port is provided at the terminal end of the tubular shaft.

12. Catheter according to claim 11, wherein the distal port is provided at the distal terminal end of the tubular shaft that contains at least one bend distal to the stop element.

13. Catheter according to claim 10, wherein an imaginary line drawn through the central axis of the distal port touches the inner surface of the tubular shaft distal of the stop element.

14. Catheter according to claim 1, configured such that the distal port is oriented to face the direction of blood flow in the sinus.

15. Catheter according to claim 1, incorporated into the sinus end of a ventriculosinus CSF shunt.

16. Catheter according to claim 1, wherein the sinus, is the superior sagittal sinus, transverse sinuses, or sigmoid sinus.

17. Catheter according to claim 1, wherein the total length of tubular shaft distal to the stop element is equal to or less than 15 mm.

18. Catheter according to claim 1, wherein the drop width of tubular shaft distal to the stop element, that is the length of the opposite side of right angled triangle, having hypotenuse (h), opposite (o) and adjacent (ad) sides, where the opposite side is opposite angle, a, where the hypotenuse (h) is the linear distance between the distal end of the tubular shaft and the point of contact with the stop element, and angle a is the corner of the triangle at said point of contact, is equal to or less than 6 mm.

19. A method for treatment of dysfunctional evacuation of cerebrospinal fluid in a subject, the method comprising inserting a catheter according to claim 1 through a wall of a dural venous sinus of the subject wherein insertion depth of the tubular shaft is limited to avoid contact of the tubular shaft with said sinus inner wall.

* * * * *